United States Patent [19]  
Duarte

[11] 4,126,144  
[45] Nov. 21, 1978

[54] PEELABLE HUMAN NAIL COATINGS

[76] Inventor: Patricia A. Duarte, 16321 Malden St., Sepulveda, Calif. 91343

[21] Appl. No.: 755,735

[22] Filed: Dec. 30, 1976

[51] Int. Cl.$^2$ .............................................. A45D 29/00
[52] U.S. Cl. ........................................ 132/73; 424/61
[58] Field of Search ........................... 132/73; 424/67; 401/122; 252/162; 156/344; 204/159.14; 159/18; 427/15, 16, 515, 543, 913

[56] References Cited

U.S. PATENT DOCUMENTS

| 2,073,867 | 3/1937 | Feigenbaum | 132/73 |
| 2,736,050 | 2/1956 | Lee | 401/122 |
| 2,764,168 | 9/1956 | Herz | 132/73 |
| 3,363,635 | 1/1968 | Wurmbock | 401/122 |

OTHER PUBLICATIONS

Dr. J. Stephan Jellinek, Formulation & Function of Cosmetics, 5/1972, pages included.

Primary Examiner—G.E. McNeil
Attorney, Agent, or Firm—Paul D. Supnik

[57] ABSTRACT

A peelable human nail coating system comprises a water emulsion of polymer resin stabilized with partially acetylated poly vinyl alcohol. The resin includes poly vinyl acetate homopolymer and poly vinyl acetate-ethylene copolymer. The composition is applied in a thin area coating drying rapidly upon exposure to air. A water impermeable clear plastic container has a restrictive wiping aperture for removing excess composition on an applicator stem to prevent dripping from the stem and caking. The composition is applied to human keratinous surfaces with a liquid absorbing applicator. After drying the coating may be removed by lifting the film at the cuticle and slowly pulling backward toward the tip of the nail. The composition is substantially odor free, contains no drying organic solvents, is generally non-toxic and non-flammable.

22 Claims, 5 Drawing Figures

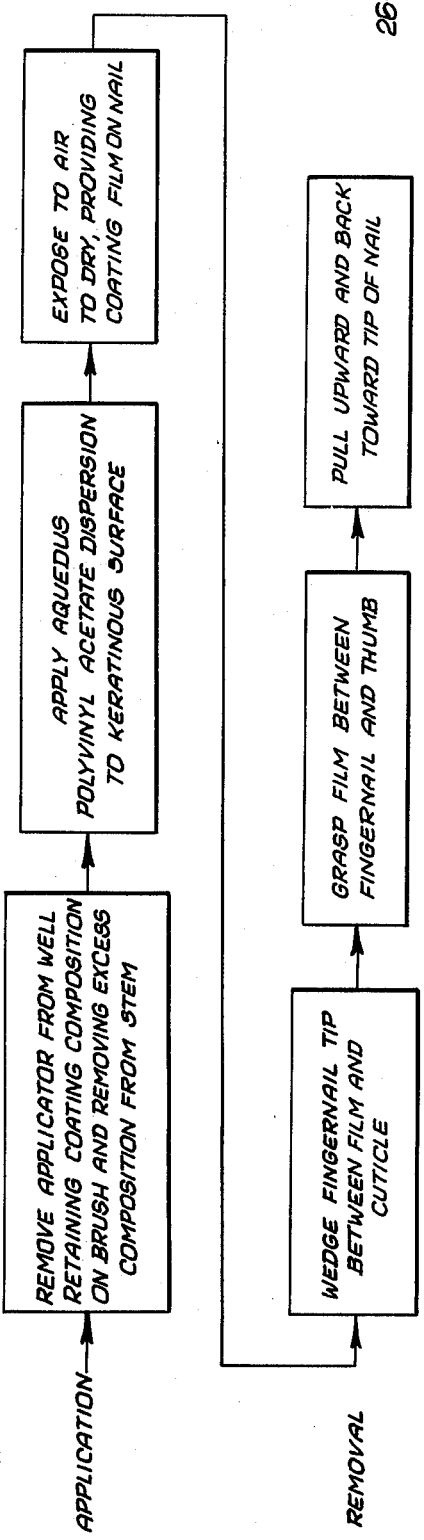
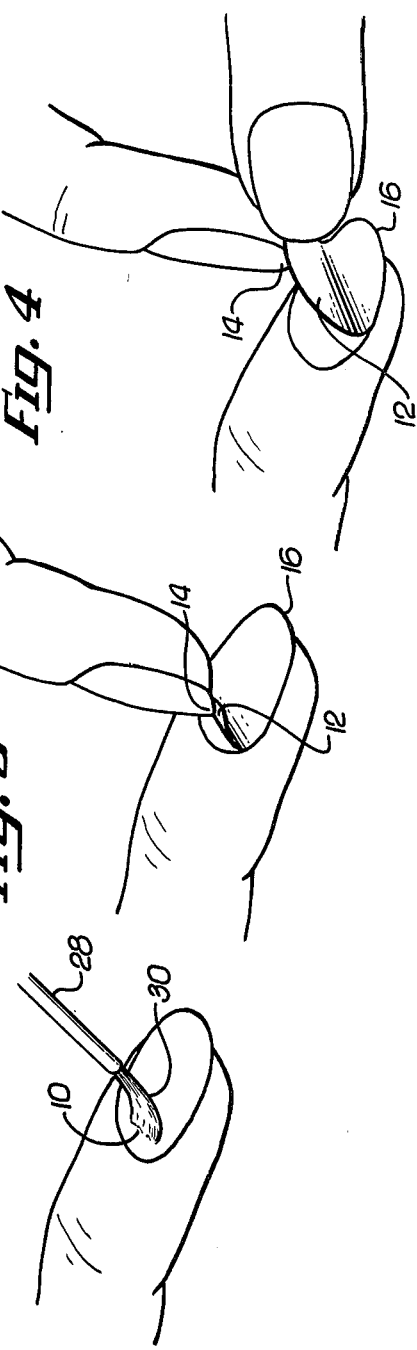

PEELABLE HUMAN NAIL COATINGS

BACKGROUND OF THE INVENTION

1. Field of the Invention

This invention relates to human nail coatings and methods for coating keratinous surfaces. More particularly, the invention relates to strippable water based fingernail coating systems.

2. Description of the Prior Art

Coatings for cosmetic purposes also known as nail polishes or nail enamels have been used for many years to provide lustrous, smooth and clear or pigmented finishes to human fingernails. It is preferable that these coatings be easily applied, have a high lustre upon drying, dry rapidly and be substantially non-toxic. Removal of nail enamels is usually messy and time consuming. Thus, it is desirable that such coatings be reasonably durable to avoid the necessity of reapplication at frequent intervals.

Nail polishes as well as base coat and top coat systems currently in use include nitrocellulose in flammable organic solvents. These polishes have an unpleasant odor and are toxic. Such polishes adhere firmly to the fingernail. Removal is commonly facilitated by organic solvents which soften and dissolve the coating. The worn or softened coatings along with the removal solvents must still be wiped or rubbed off the nail. The polish removers also have unpleasant, penetrating odors, are toxic and flammable. In addition, the use of such compositions may cause damage to the nail and cuticle. Organic solvents tend to defat and thereby dry the nails which may then become brittle and unsightly. Nail polishes are commonly sold in glass containers as they have a tendency to react with many types of plastics. Because of shipping weight and marketability, it would be desirable to package nail polishes in clear plastic containers.

Efforts to mitigate some of these problems have been described such as by precoating the nail with a base comprising a film forming resin compound which includes a vinyl chloride-vinyl acetate copolymer as described in U.S. Pat. No. 2,764,168, issued Sept. 25, 1956 to Benno Herz. After the nail is precoated with such a solution and allowed to set, an ordinary nitrocellulose lacquer based fingernail polish is applied. The nail polish is said to be removable from the base without use of solvents, however, such compositions require an inconvenient and time consuming two-step process.

Another multicoat process and composition is described in U.S. Pat. No. 3,928,113, Rosenberg, issued Dec. 23, 1975 in which a base coat of a composition comprising a water soluble or water swellable polymer dissolved in a solvent is first applied to the nail and is allowed to dry. Thereafter, a photocurable polymer composition is applied to the precoated nail and is then exposed to a light source to set the photocurable polymer. This process is time consuming, requiring exposure to light for curing as well as two distinct applications. Removal requires soaking in water followed by wiping or rubbing off the worn polish.

SUMMARY

A peelable nail coating composition in accordance with this invention consists essentially of an aqueous dispersion of a latex polymer. Both poly vinyl acetate homopolymer resin and poly vinyl acetate-ethylene copolymer resin may be used. An additional substance is included in the composition to suspend the resin in water.

In a more specific example, the peelable aqueous composition comprises a resin solids content of between about 40% by weight and about 50% by weight of the composition. The dispersion is stabilized in water by the inclusion of partially acetylated poly vinyl alcohol.

A nail coating system in accordance with the invention includes the aforementioned composition disposed in a receptacle well of a sealable container. The container includes a closable cap having a stem which extends into the well to receive the liquid composition. In some forms of the coating system, the receptacle includes a wiper aperture to remove excess composition covering the stem as the stem is pulled out from the receptacle.

Additional features of the composition may include the addition of a substantially water insoluble pigment material comprising not more than about 15% by weight of the composition. In addition, limited quantities of anti-microbial agents may be added, as well as wetting agents, anti-foaming agents and ultra violet light absorbing agents.

The method for removing the coating once it has been applied and dried includes wedging a fingernail between the cuticle and the coated film, grasping the film and lifting away from the base of the nail and back towards the tip of the nail. There is no need for solvents or soaking in liquids to remove the coating.

BRIEF DESCRIPTION OF THE DRAWINGS

The nature of the invention described herein may be best understood and appreciated by the following description taken in connection with the accompanying drawings in which:

FIG. 1 is a block diagram of a method for applying and thereafter removing a human nail coating in accordance with this invention;

FIG. 2 is a perspective view depicting the application of the new coating composition to a human nail in accordance with this invention;

FIG. 3 is a perspective view depicting a human fingernail wedged between the cuticle and the coated film depicted in FIG. 2 for peeling the coated film from the fingernail in accordance with the method of this invention;

FIG. 4 is a perspective view depicting the human fingernail shown in FIG. 3 in which the coated film has been partially removed in accordance with this invention; and FIG. 5 is an exploded perspective view with portions exposed and portions removed of a nail polish system including a container and a coating composition in accordance with this invention.

DETAILED DESCRIPTION

The human nail composition in accordance with this invention comprises an aqueous dispersion of a latex polymer. As used herein, the term latex polymer indicates a synthetic milky resinous water dispersion which dries on exposure to air. Latex polymer for purposes of this discussion is typified by either a poly vinyl acetate homopolymer resin or a poly vinyl acetate-ethylene copolymer resin.

A poly vinyl acetate-ethylene copolymer resin is defined as having on the average not more than about 50% ethylene radicals per copolymer molecule.

Poly vinyl acetate homopolymer resin is commonly available commercially as an aqueous dispersion of about 50% to 55% by weight solids content, typically stabilized with partially acetylated poly vinyl alcohol, believed not to exceed more than about 2% by weight of the emulsion. Similarly, poly vinyl acetate-ethylene copolymer emulsion is also stabilized with partially acetylated poly vinyl alcohol. It is believed that the percentage of acetyl radicals within the partially acetylated poly vinyl alcohol molecules do not exceed about 20%. In addition both poly vinyl acetatee homopolymer and poly vinl acetate-ethylene copolymer are also available in solid form such as powders.

The word emulsion as used herein means a liquid preparation consisting of minute particles of a resinous substance held in suspension in an aqueous fluid by means of a viscous matter, in this case primarily partially acetylated poly vinyl alcohol or a surfactant. The word dispersion is intended to be interchangeable with the definition of emulsion as used herein.

The term nail polish is used to indicate a liquid which is applied to the human keratinous tissue such as fingernails to impart usually, though not always, a lustrous finish or a protective finish to nails. The term is also used in a broader sense to refer to a base coat to human keratinous surfaces upon which other coats may be applied.

The words consisting essentially of means that the composition referred to may consist entirely of or include certain other constituents not specifically mentioned in addition to the components specified. Thus, certain components such as natural or synthetic resins, gums, clays, waxes and rosins, plasticizers, alcohols, glycols, triols and polyols, preservatives, whether antioxidants or antimicrobials, antifoam agents, protein and protein derivatives can be added in limited quantities. Ultraviolet light absorbers and surface active agents may also be included in such compositions.

The term solids content refers to the percentage of specific polymer by weight to the total weight of the composition or constituent.

Examples of aqueous dispersions of polyvinyl acetate homopolymer include Vinac XX-230, Vinac 881 and Gelva homopolymer. Vinac is a registered trademark of Air Products & Chemical Co., Wayne, Penn., Gelva is a registered trademark of Monsanto Company. Examples of poly vinyl acetate-ethylene copolymer dispersions include Airflex 100HS. Airflex is a registered trademark of Air Products and Chemical Co.

Examples of acrylic polymers which may be substituted for poly vinyl acetate homopolymers, or poly vinyl acetate-ethylene copolymers in limited quantities (up to about 5%) in the compositions described herein include Rhoplex C-72. Rhoplex is a registered trademark of Rohm and Haas Company, Philadelphia, Penn.

In accordance with this invention, the following examples were found to provide a satisfactory peelable nail coating.

| Components: | Parts by Weight | | |
|---|---|---|---|
| | Example 1 | Example 2 | Example 3 |
| Polyvinyl acetate homopolymer emulsion | 100 | 40 | 0 |
| Polyvinyl acetate-ethylene copolymer emulsion | 0 | 60 | 100 |

In examples 1, 2 and 3, the solids content of polymer resin is typically 50%-55% depending on the grade of poly vinyl acetate or acetate-ethylene used. When other constituents are added, the solids content drops to a preferred content of 40% by weight to 50% by weight.

Small particle size emulsions generally impart flexibility, surface shine and peelability while large particle size emulsions provide increased viscosity and improved durability. Certain other latex dispersions may be added to modify the properties of the compositions somewhat. Thus, in examples 5 and 6, aqueous acrylic polymer emulsion was used in limited quantities still resulting in a peelable finish.

| Components: | Parts by Weight | | |
|---|---|---|---|
| | Example 4 | Example 5 | Example 6 |
| Airflex 100HS | 50 | 65 | 60 |
| Vinac XX-230 | 30 | 30 | 15 |
| Vinac 881 | 20 | | 23 |
| Rhoplex C-72 | | 5 | 2 |

Characteristic of the dried films on keratinous surfaces is that they are not readily dispersed in water. The keratinous surface is sufficiently pourous to promote adhesive bonding and for this reason makes the surface unsuitable for use with substantial concentrations of other resins.

The dried films on the nail usually have a lustrous and smooth finish. Uniformity upon application of a single coat without a trace of brushmarks for examples given herein is typical. The films are water resistant, even though the original dispersion is water based. All of the above examples resulted in compounds which were easily peelable.

Following initial experimentation it was found that the following examples of coating composition containing as little as 35% solids content (Example 7) and as much as 60% solids content (Example 8) still provided strippable fingernail coatings. However, Example 7 provided a slow drying composition while Example 8 provide a rapid drying composition.

| Component: | Example 7 | Example 8 |
|---|---|---|
| Poly vinyl acetate homopolymer emulsion | 30 grams | 10 grams |
| Poly vinyl acetate homopolymer solids | | 15 grams |
| Poly vinyl acetate-ethylene copolymer emulsion | 70 grams | 70 grams |
| Water | 45 grams | |

In some peelable coating compositions the viscosity may be varied by the addition of natural or synthetic resins, gums, clays, waxes and rosins in limited quantities. Plasticizers can be used to unify and add ruggedness to the film, such as sold under the trademark Hercoflex 900 of Hercules Corporation. Alcohols, glycols, triols and polyols may be added to increase softness and improve the ductility of the film. Preservatives may be added, both as antioxidants and antimicrobials, to prevent the growth of undesirable and unsanitary organisms.

Pigments, dyes and coloring agents may be added to impart color to the coating. It is preferable that these materials be substantially water insoluble to avoid staining of the keratinous tissue.

Example 9 provided a pigmented coating composition. The nacreous pigment used in Example 9 is a titanium coated mica and may be purchased under the trademark of Timica Bronze of Merle Corporation. Since the pigment is a substantially non-reactive solid component of the composition, rather large amounts of pigment may be used, in this example 15% by weight.

EXAMPLE 9

| Poly vinyl acetate homopolymer emulsion | 10 grams |
|---|---|
| Poly vinyl acetate-ethylene copolymer emulsion | 75 grams |
| Nacreous pigment | 15 grams |

The coating is best applied without formation of bubbles. This requires that bubbles not develop and cling to the applicator. For this reason, it may be desirable to add an antifoam agent such as sold under the trademark Dow Corning Anti-Foam A. Protein and protein derivatives may be added to the composition such as sold under the trademark Anti-Foam B of Dow Corning.

The sun may have an adverse drying effect on the skin and also results in bleaching of pigmented coatings and deterioration of the nail coatings. Thus ultra violet light absorbers such as para-amino benzoic acid or its esters may be added such as sold under the trademark of Escarol by Van Dyk corporation.

Although partially acetylated poly vinyl alcohol is a preferred dispersing agent, other surface active agents may be added to improve uniform spreadability of the coating on nails.

The composition may be acid balanced for compatibility with human skin by additions of small amounts of acids or alkalis to bring the pH of the composition to about 3 to about 6.

With particular reference to the drawings, FIG. 1 and FIG. 2 depict the method for applying a coating composition in accordance with this invention. The coating composition 10 is typically brushed on in a single application. The coating dries rapidly, typically forming a dry film 12 within about 1 minute. It may thereafter be removed when desired by wedging a fingernail tip 14 between the film and the inner region of the cuticle. The film 12 is then grasped between the wedged fingernail and preferably the thumb or the index finger. The film is then removed by pulling upward and back toward the tip 16 of the coated nail as depicted in FIG. 4. This application procedure can be performed very quickly in a single coat. Yet the removal procedure is fast, does not require the use of organic solvents harmful to the nails and cuticle nor does it even require soaking in water. Depending on the particular composition, the film may not come off in one piece though is still readily peelable.

A fingernail coating system in accordance with this invention is best described with reference to FIG. 5. A sealable container 18 comprises a liquid receptacle 20 which may be either of a water impermeable plastic or glass. Suitable plastic materials include PVC and SAN. Clear plastic allows the colors of the composition when pigmented to be visible. The receptacle has a well having the coating composition 10 therein. At the upper end of the bottle an apertured plug or wiper 22 such as of polyethylene or other suitable material is fitted in the neck of the receptacle and includes an annular ledge 24 which rests on a circular mouth of the receptacle. The container 18 includes a cap 26 having a stem 28 extending therefrom which includes a brush applicator tip 30 at its end. A porous foam or other type of suitable applicator tip may also be used. The cap 26 has an inner thread 32 which mates with an outer thread 34 on the receptacle 20. When the cap 26 mates with the receptacle, the applicator tip is disposed within the receptacle well. The stem 28 defines a nominal cross sectional area. An access opening approximately the same as the nominal cross sectional area of the stem 28 prevents the buildup of excess composition covering the stem 28 when it is removed from the well. The composition 10 dries quite rapidly and though the wiper 22 is not necessary, it does help prevent dripping from and caking on the stem. Typically, the size of the well, as a practical matter is less than about 15 cc, avoiding the problems of having the contents dry out before the composition is substantially depleted.

Although the invention has been described with reference to specific forms thereof, it will be understood that changes and modifications may be made within the spirit of this invention.

What is claimed is:

1. A nail coating system for use in applying films to human nails comprising:

a sealable container including a liquid receptacle defining a well, a liquid nail coating composition within the well and a closable cap mating with the liquid receptacle to seal the well from the atmosphere, the cap including means extending into the well for receiving the liquid nail coating composition and for applying the composition to a keratinous surface; and in which the liquid nail coating composition comprises an aqueous latex polymer emulsion, the emulsion comprising poly vinyl resin having a solids content of between about 35% by weight to about 60% by weight of the emulsion, the poly vinyl resin selected from the group consisting of poly vinyl acetate homopolymer resin and poly vinyl acetate ethylene copolymer resin.

2. The invention as set forth in claim 1 and in which the emulsion is an aqueous dispersion comprising not more than about 2% by weight of partially acetylated poly vinyl alcohol resin solids.

3. The invention as set forth in claim 2 and in which the resin solids comprise between about 40% by weight to about 50% by weight of the composition.

4. The invention as set forth in claim 3 and comprising an essentially water insoluble pigment material dispersed within the emulsion.

5. A human nail coating system for use in applying a lustrous finish to keratinous surfaces comprising:

a sealable container including a liquid receptacle defining a well, a closable cap mating with the liquid receptacle to seal the container from the atmosphere, the cap including a stem extending into the well when the cap mates with the liquid receptacle, the stem including an applicator tip for receiving a nail coating composition when disposed within the well;

a human nail coating composition disposed within the well, the composition comprising an aqueous dispersion of latex polymer selected from the group consisting of poly vinyl acetate homopolymer resin and poly vinyl acetate-ethylene copolymer resin, said latex polymer having a solids content from about 40% by weight to about 50% by weight of the composition, the composition comprising means for stabilizing the resin dispersion in water.

6. The invention as set forth in claim 5 and in which the composition comprises partially acetylated poly vinyl alcohol having a solids content not exceeding about 2% by weight of the composition; and a substantially water insoluble pigment dispersed within the composition and having a solids content not exceeding 15% by weight of the composition.

7. The invention as set forth in claim 5 and in which the receptacle comprises wiper means partially enclosing the well and defining an aperture for receiving the stem of the cap, the stem defining a nominal cross sectional area, the aperture providing an access opening approximately the same as the nominal cross sectional area of the stem so that excess composition covering the stem when the stem is in the well is substantially removed as the stem is pulled out from the receptacle, the composition drying rapidly upon exposure to air and the wiper means preventing excess composition from drying on the stem; and in which the well having a liquid capacity of less than about 15 cc.

8. The invention as set forth in claim 5 and in which the receptacle comprises a substantially water impervious plastic material.

9. A nail coating composition for providing a strippable finish to a keratinous surface, the composition consisting essentially of:

an aqueous dispersion of resin selected from the group consisting of poly vinyl acetate homopolymer resin and poly vinyl acetate-ethylene copolymer resin and comprising means for suspending the resin in water.

10. The nail coating composition as set forth in claim 9 and in which the resin solids consist of approximately 40% by weight to about 50% by weight of the composition.

11. The nail coating composition as set forth in claim 10 and comprising partially acetylated poly vinyl alcohol constituting less than about 2% solids by weight of the composition to stabilize the dispersion in water and the composition comprising an anti-microbial agent to prevent undesirable growths.

12. The nail coating composition as set forth in claim 10 and comprising a substantially water insoluble pigment material not exceeding 15% by weight of the total composition.

13. A human nail coating composition comprising a blend of at least 30% by weight of a partially acetylated poly vinyl alcohol stabilized aqueous dispersion of poly vinyl acetate homopolymer and at least about 50% by weight of an aqueous dispersion of poly vinyl acetate-ethylene copolymer having a solids content on the order of 50% by weight, the composition having a pH of from about 3 to about 6, the homopolymer and copolymer solids content having an average molecular size on the order of 0.1 micron.

14. The nail coating composition as set forth in claim 13 and comprising a substantially water insoluble pigment comprising not more than about 15 parts by weight of the total composition.

15. The composition as set forth in claim 14 and comprising a wetting agent and an anti-foaming agent.

16. The composition as set forth in claim 15 and comprising a sunscreen agent and an antimicrobial agent.

17. A method for imparting a strippable coating to a human nail comprising the steps of:

applying a water based nail polish composition to a keratinous surface, the composition comprising a stabilized latex polymer dispersion, the dispersion comprising resin selected from the group consisting of poly vinyl acetate homopolymer and poly vinyl acetate-ethylene copolymer; and exposing the applied composition to air for about 1 minute.

18. The method as set forth in claim 17 and in which the composition comprises between about 35% by weight to about 60% by weight resin solids and the composition comprises a stabilizing agent so that the dispersion is uniformly spreadable over the keratinous surface.

19. The method as set forth in claim 18 and in which the composition comprises from about 40% by weight to about 50% by weight resin solids and including poly vinyl alcohol to stabilize the dispersion in water; and comprising the steps of placing an applicator tip in a well containing the coating composition;

removing the applicator tip from the well, the tip retaining some of the liquid composition thereon; and applying the applicator tip to the keratinous surface of the human nail.

20. A method for applying and removing a nail polish coating comprising the steps of:

applying a water based nail coating composition to a keratinous surface, the composition comprising a vinyl acetate resin having a solids content of between 35% by weight and 60% by weight, the vinyl acetate resin selected from the group consisting of poly vinyl acetate homopolymer and poly vinyl acetate-ethylene copolymer, the composition containing a stabilizing agent so that the nail coating is uniform on application;

exposing the nail to air for in excess of about five minutes; and thereafter removing the coating when desired by lifting the dried coating from the cuticle of the nail and pulling the coating off the nail.

21. The method as set forth in claim 20 and in which the composition comprises between about 40% by weight to about 50% by weight resin solids, and the method comprises the steps of placing an applicator having a brush tip in a well containing the coating composition, removing the applicator tip from the well, the tip retaining some of the liquid composition thereon and brushing the composition on the keratinous surface in a single application to provide a smooth uniform coating.

22. The method as set forth in claim 21 and in which:

a portion of the liquid on the applicator is removed from the applicator prior to brushing the composition on the keratinous surface; and the step of removing the coating from the keratinous surface comprises the step of wedging a fingernail between the inward region of the base of the coated nail and the dried coating, grasping the film by said fingernail and a different finger and pulling the coating away from and back toward the tip of the coated nail to lift the coating off the keratinous surface.

* * * * *